United States Patent [19]

Assa

[11] Patent Number: 5,240,011
[45] Date of Patent: Aug. 31, 1993

[54] MOTORIZED BIOPSY NEEDLE POSITIONER

[75] Inventor: Michael Assa, Englewood, Colo.

[73] Assignee: Fischer Imaging Corporation, Denver, Colo.

[21] Appl. No.: 799,418

[22] Filed: Nov. 27, 1991

[51] Int. Cl.$^5$ ............................................. A61B 6/00
[52] U.S. Cl. .................................. 128/751; 606/130; 606/167; 128/755
[58] Field of Search ................................ 128/751–755; 606/167–170

[56] References Cited

U.S. PATENT DOCUMENTS

| 4,791,934 | 12/1988 | Brunnett | 606/130 |
| 4,890,311 | 12/1989 | Saffer | 378/99 |
| 4,958,625 | 9/1990 | Bates et al. | 128/754 |

OTHER PUBLICATIONS

"Stereotaxic Instrument for Needle Biopsy of the Mamma," Bolingren, Tan et al, *American Journal Roentgenology*, vol. 129 pp. 121–125, 1977.

*Primary Examiner*—Lee S. Cohen
*Assistant Examiner*—Robert L. Nasser, Jr.
*Attorney, Agent, or Firm*—Sheridan, Ross & McIntosh

[57] ABSTRACT

A motorized biopsy needle positioner employed in a mammographic needle biopsy system receives coordinate information representative of a previously identified point of interest within a patient's captive breast under examination and automatically positions a biopsy needle in accordance with that coordinate information to permit insertion of the biopsy needle to the previously identified point of interest. An offset mode of operation of the motorized biopsy needle positioner automatically positions the biopsy needle in accordance with coordinate information representative of an offset point within the patient's breast that is offset from the previously identified point of interest to permit insertion of the biopsy needle to that offset point. A manual mode of operation of the motorized biopsy needle positioner permits the user to actuate directional keys of a user control unit to position the biopsy needle in one or more directions, as specified by the actuated directional keys.

12 Claims, 6 Drawing Sheets

MOTORIZED BIOPSY NEEDLE POSITIONER

REFERENCE TO RELATED PATENT

This application is related to allowed U.S. patent application Ser. No. 07/440,775 entitled Precision Mammographic Needle Biopsy System now U.S. Pat. No. 5,078,142, the subject matter of which is incorporated herein by reference.

BACKGROUND AND SUMMARY OF THE INVENTION

This invention relates generally to medical mammography systems that are designed to detect and biopsy non-palpable lesions of the female breast. More particularly, this invention is directed to a motorized biopsy needle positioner that automatically positions a biopsy needle to allow insertion to a previously identified point of interest in a patient's breast that is under examination.

Known mammographic needle biopsy systems, such as the Mammotest system manufactured and marketed by Fischer Imaging Corporation, Denver, Colorado, employ a computer-digitizer system to digitize the location of a point of interest within the patient's breast as that point of interest appears on a pair of stereo x-rays of the breast and to thereafter compute the three-dimensional or spatial coordinates of that point of interest and display them to the user. The user then manually sets these three-dimensional coordinates into respective position controls of a puncture instrument and inserts a biopsy or other needle to the identified point of interest. These manual systems are susceptible to human error in setting the computed coordinates of the point of interest into the puncture instrument. In addition, manual setting of the coordinates of the point of interest is a time consuming operation that is frustrating to the patient, who is required to continue holding a position in which one of her breasts is under compression. Also, the clinician user of these prior art mammographic biopsy systems is not permitted the flexibility of inserting the biopsy needle to a point within the patient's breast that is slightly offset from the previously identified point of interest because the coordinates provided by the computer-digitizer correspond precisely to the idenified point of interest.

It is therefore a principal object of the present invention to provide a motorized biopsy needle positioner for mammographic needle biopsy systems that automatically positions a biopsy needle to permit insertion of the needle to a previously identified point of interest within a patient's breast.

It is a further object of the present invention to provide a motorized biopsy needle positioner for mammographic needle biopsy systems that includes a control unit for enabling the user to automatically position a biopsy needle to allow insertion of the needle to a point within a patient's breast that is spatially offset from a previously identified point of interest.

DETAILED DESCRIPTION OF THE INVENTION

Figure 1:
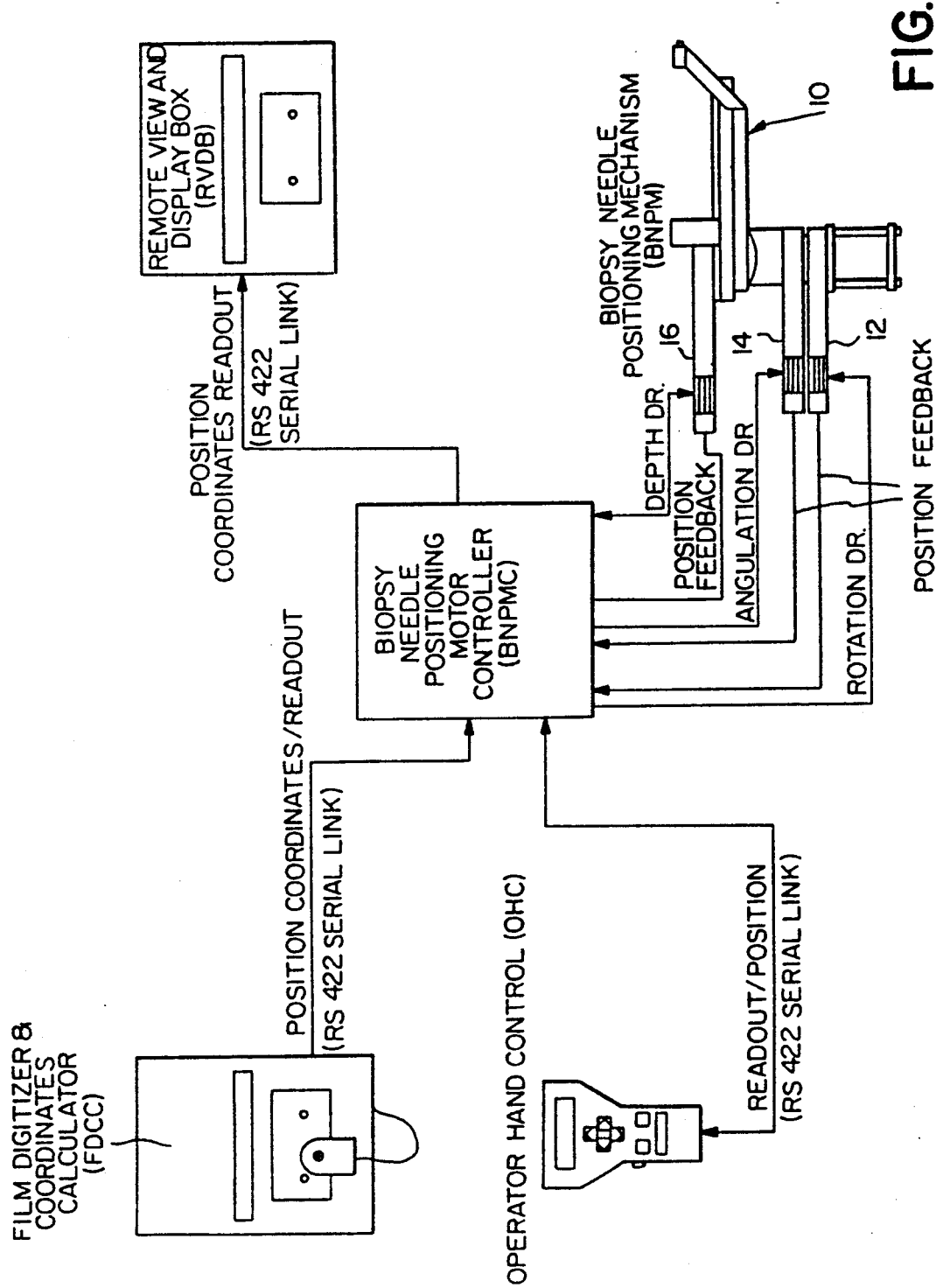
FIG. 1 is an overall block diagram of the motorized biopsy needle positioner of the present invention.

Referring now to the block diagram of FIG. 1, there is shown a motorized biopsy needle positioner that includes a film digitizer and coordinates calculator FDCC, a biopsy needle positioning motor controller BNPMC, a biopsy needle positioning mechanism BNPM, an operator hand controller OHC, and a remote view and display box RVDB. The film digitizer and coordinates calculator operates conventionally in accordance with the teachings of the reference cited above, for example, to digitize a point of interest in a patient's breast under examination and to thereafter compute and display the three-dimensional or spatial coordinates of the digitized point of interest. While the three-dimensional or spatial coordinates of the point of interest are expressed as polar coordinates in the embodiment described herein, they may also be expressed as coordinates in an X, Y, and Z rectangular coordinate system.

The biopsy needle positioning motor controller receives the computed spatial coordinates of an identified point of interest from the film digitizer and coordinates calculator and drives three conventional DC motors motors that serve to control a puncture instrument in its rotation (horizontal) and angulation (vertical) axes, and to set a stop position along its depth axis to position a biopsy needle or other device retained by the puncture instrument for insertion to the identified point of interest within the patient's breast.

Figure 2:
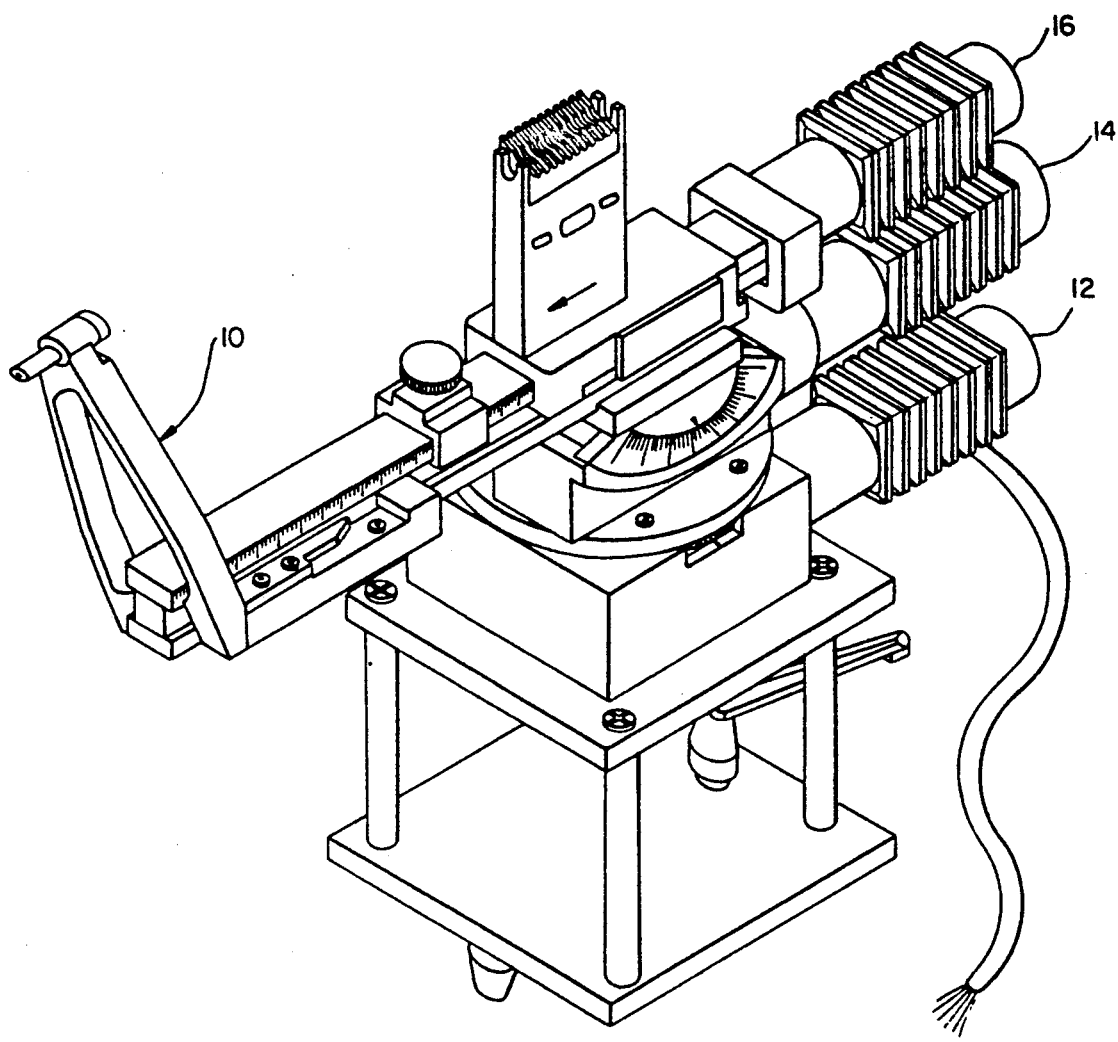
FIG. 2 is a pictorial diagram illustrating the biopsy needle positioning mechanism employed in the motorized biopsy needle positioner of FIG. 1.

The biopsy needle positioning mechanism, illustrated in the detailed diagram of FIG. 2, and typically employed as a component of an overall mammographic needle biopsy system, comprises a conventional puncture instrument 10 for retaining a biopsy needle or other biopsy or therapeutic delivery device (not illustrated). Three conventional DC motors 12, 14, and 16 are provided for moving the biopsy needle retained by the puncture instrument 10 in the rotation and angulation axes and for setting a stop position along the depth axis, respectively. Positional feedback is provided to the biopsy needle positioning motor controller by the three DC motors 12, 14, and 16.

The operator hand controller allows the clinician user to control the motorized biopsy needle positioning system. Controls are provided to permit the user to initiate movement of the biopsy needle into a position for insertion to the identified point of interest within the patient's breast, in accordance with the computed spatial coordinates of that point of interest. The position of the biopsy needle may be monitored by the user with reference to a 32-character display on the operator hand controller. An enable switch is provided to prevent inadvertent motion of the biopsy needle.

The remote view and display box receives the spatial coordinates of rotation, angulation, and depth from the biopsy needle positioning motor controller and displays them for the benefit of the clinician user or others on a 40-character alphanumeric display. The remote view and display box may be conveniently mounted on a table that includes means for mounting and lighting x-ray reference films to be viewed during a breast biopsy procedure.

Figure 3:
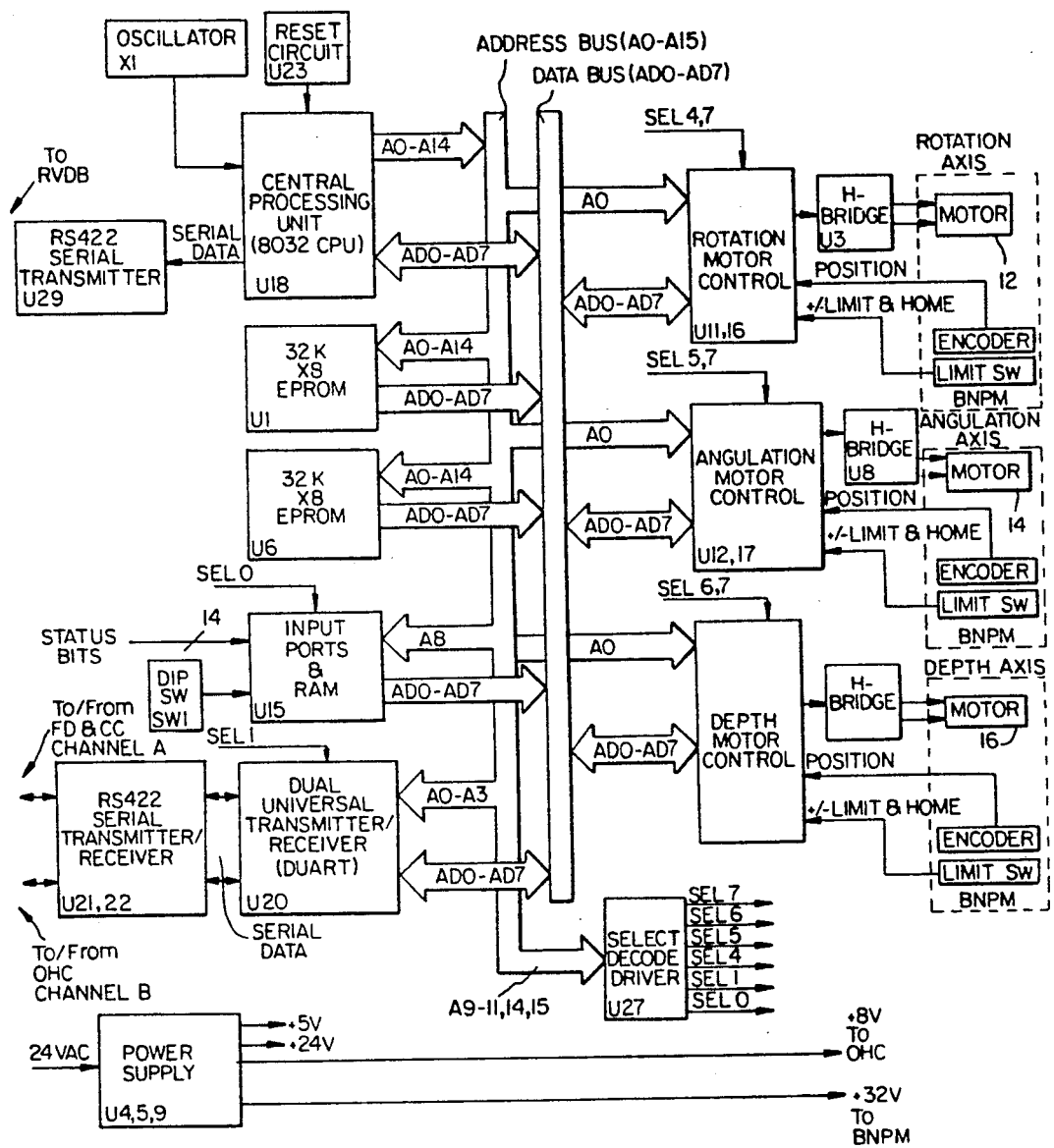
FIG. 3 is a detailed block diagram of the biopsy needle positioning motor controller of FIG. 1.

Operation of the biopsy needle positioning motor controller may be understood with reference to the detailed block diagram of FIG. 3. The biopsy needle positioning motor controller receives the spatial coordinates of the identified point of interest within the patient's breast from the film digitizer and coordinates calculator and computes the variables required to drive the three DC motors 12, 14, and 16 that form part of the biopsy needle positioning mechanism. Information regarding the position of the biopsy needle is continuously provided by the biopsy needle positioning motor controller to the LED displays in the operator hand controller. During manual operation, the biopsy needle positioning motor controller receives commands from the operator hand controller and drives the biopsy needle positioning mechanism in the direction specified for as long as the user simultaneously depresses one of the direction arrow keys and the enable switch located on the operator hand controller illustrated in FIG. 4.

A central processing unit (8032 CPU) within the biopsy needle positioning motor controller has a direct serial communications link with the remote view and display box through an RS422 serial transmitter U29. The 8032 CPU also has two bi-directional communications links through a dual asynchronous universal transmitter/receiver DUART, which provides serial communications between the biopsy needle positioning motor controller and both the film digitizer and coordinates calculator (serial channel B) and the operator hand controller (serial channel A).

Under normal operating conditions, the 8032 CPU loads the three DC motor controller sections (rotation, angulation, and depth) with high level initial conditions data. This initial conditions data includes velocity constants, acceleration constants, PID filter information, and sample period. When the spatial coordinates of the identified point of interest within the patient's breast, as computed by the film digitizer and coordinates calculator, are placed on the data bus AD0-AD7 by DUART U11, the 8032 CPU reads these spatial coordinates and calculates the corresponding motor control values. The 8032 CPU then sends this data to the three motor control sections. The motor control sections calculate the actual motor drive voltages and provide the drive voltages to motors 12, 14, and 16 through separate H-bridge circuits. The motor control sections monitor the encoder feedback from the biopsy needle positioning mechanism to determine the position of the biopsy needle and to adjust the motor drive voltages as the biopsy needle reaches the identified point of interest. A typical motor voltage and velocity profile is trapezoidal in nature, ramping up to a start voltage, then holding constant, and finally ramping down to a stop voltage when the biopsy needle has reached the position required for insertion to the identified point of interest.

The 8032 CPU support circuits include operating and debug program data in erasable programmable read-only memories EPROMs U1 and U6. Fourteen status bits plus a six-bit DIP switch are monitored through an input port and a random access memory RAM U15. The status bits include ± limit switches and a home switch associated with each coordinate axis. Two additional status bits serve to monitor the +5-volt (+5ENC) and +24-volt (+24VOK) power supplies. A reset circuit U23 provides a reset signal to reset the 8032 CPU when power is initially applied. The reset circuit also monitors program execution by counting a pulse associated with each cycle of the program and by executing a CPU reset command if the pulses stop, as may occur during a software lockup.

Figure 4:
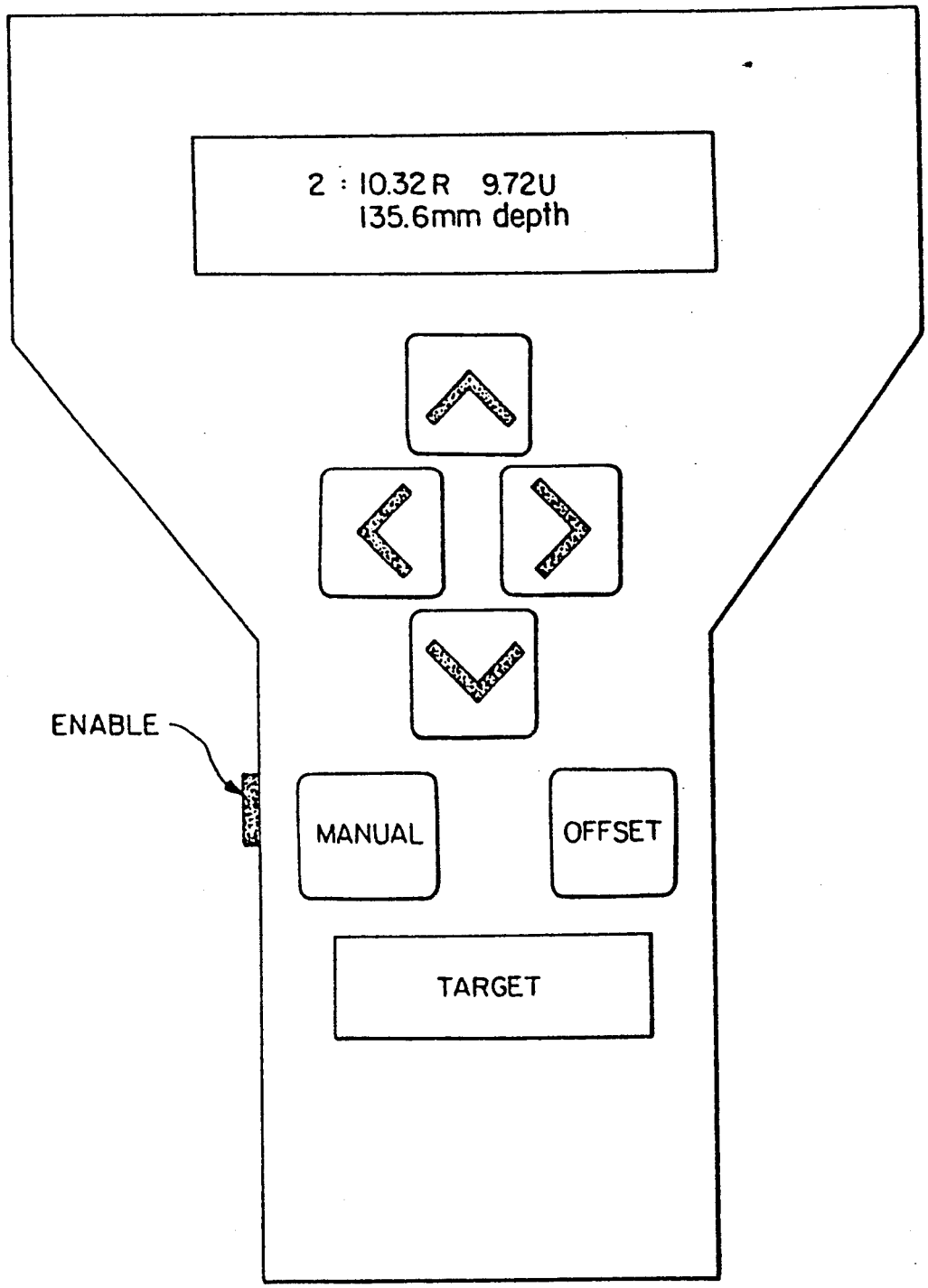
FIG. 4 is a pictorial diagram of the operator hand controller of FIG. 1.
Figure 5:
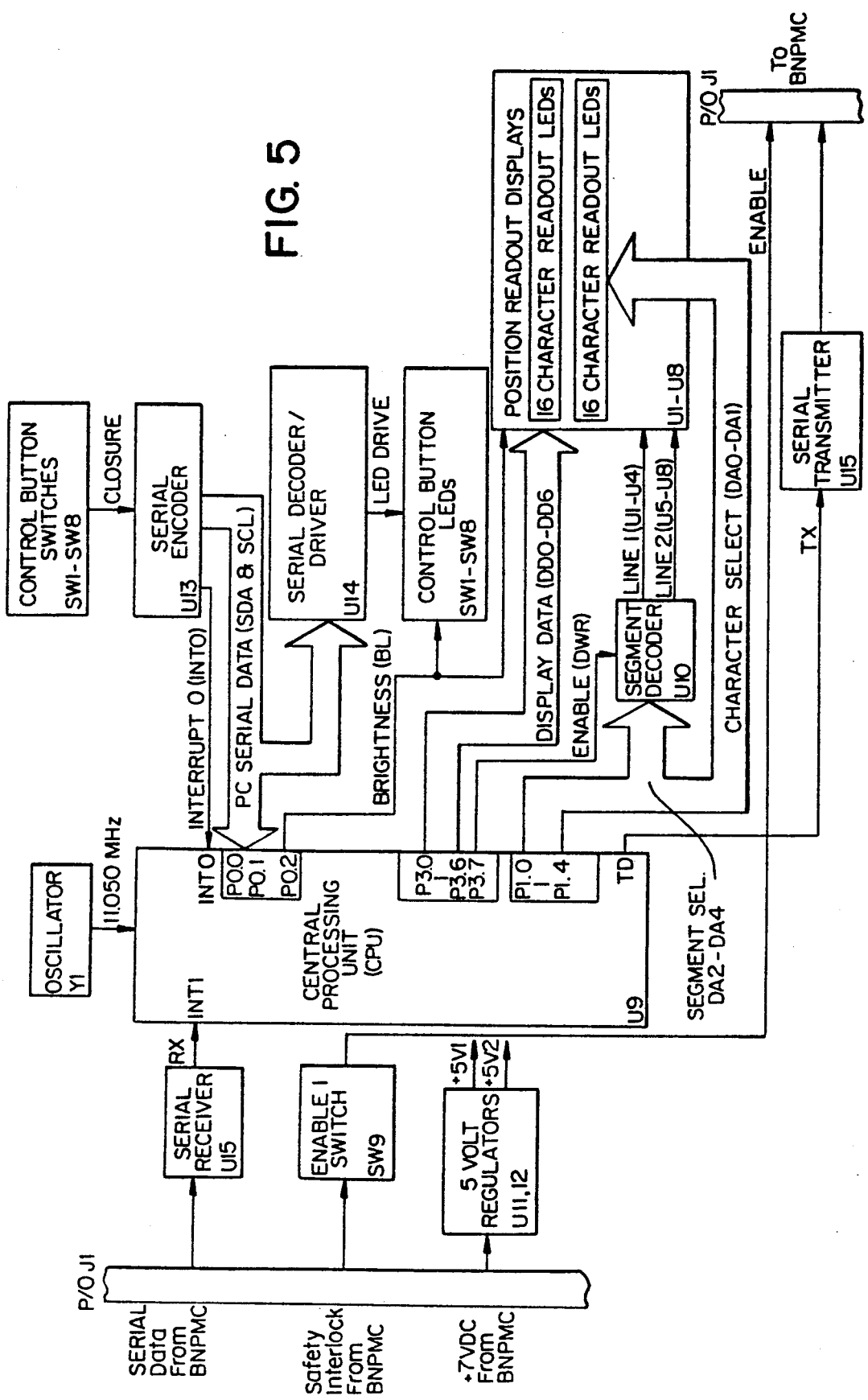
FIG. 5 is a detailed block diagram of circuitry employed in the operator hand controller of FIGS. 1 and 4.

Referring now to FIGS. 4 and 5, it will be understood how the operator hand controller of FIG. 4 transmits data to and receives data and instructions from the biopsy needle positioning motor controller via an RS422 serial transmitter/receiver bus (serial channel A). While the operator hand controller is described herein as being a hand-held unit, it may also comprise a console or table-mounted unit. The principal functions of the operator hand controller are to 1) transmit switch closure data resulting from actuation of the direction arrow keys and the MANUAL, OFFSET, and TARGET keys to the biopsy needle positioning motor controller; 2) illuminate button LEDs in accordance with information received from the biopsy needle positioning motor controller; and 3) display the spatial coordinates of the identified point of interest within the patient's breast, as provided by the biopsy needle positioning motor controller. Additionally, the operator hand controller provides a safety interlock through the ENABLE switch SW9, which must be simultaneously depressed by the user with a selected one of the function keys in order to initiate any of the functions of the operator hand controller. The ENABLE switch is mounted on the side of the operator hand controller and, when depressed, energizes a relay in the biopsy needle positioning motor controller that enables movement of the biopsy needle positioning mechanism. When this switch opens, the relay removes power from the three DC motors 12, 14, and 16 of the biopsy needle positioning mechanism.

The clinician user initiates control of the biopsy needle positioning mechanism in either an automatic or manual mode by depressing control switches on the operator hand controller. Depressing one of the arrow keys or one of the MANUAL, OFFSET or TARGET keys has the effect of grounding a corresponding input of serial encoder U13. This causes serial encoder U13 to apply an INTERRUPT 0 (INT00) to the CPU U9 and place the serial data in I²C protocol on the serial lines SDA and SCL to the CPU U9. The CPU U9 converts the switch information to RS422 protocol and sends it to the biopsy needle positioning motor controller via serial transmitter U15. Each of the keys on the operator hand controller contains a light emitting diode LED that is illuminated under the control of the biopsy needle positioning motor controller. The biopsy needle positioning motor controller selects a particular LED to be illuminated, sets the brightness of that LED, and determines how long that LED is to remain illuminated. This information is sent to the -CPU U9 via serial receiver U15. The CPU U9 then places the information in I²C protocol on the serial lines SDA and SCL to be transmitted to serial decoder/driver U14. Serial decoder/driver U14 pulls a corresponding output to its low state, thereby illuminating the selected LED. The CPU U9 controls the brightness of the LEDs on the operator hand controller by setting the duty cycle of BRIGHTNESS (BL) pulses applied to the LEDs. A 50% duty cycle illuminates the LEDs at half brightness and a 100% duty cycle illuminates the LEDs at full brightness.

The position readout displays U1-U8 in the operator hand controller provide two rows of displayed information comprising 16 ASCII characters in each row. Each row comprises four display devices, and each display device contains four 5×7 dot matrix character displays. Referring to FIG. 4, the top line of the position readout display indicates target number 2 (2:), a rotation axis angle of 10.32 degrees right (10.32R), and an angulation axis angle of 9.72 degrees up (9.72U). The bottom line of the postion readout display indicates a depth stop setting of 135.6 millimeters (135.6mm depth). As previously described in connection with the LEDs that illuminate each of the keys of the operator hand controller, the biopsy needle positioning motor controller similarly controls the position readout displays through serial communications with the operator hand controller CPU U9. The CPU U9 provides segment selection control and character display using two data buses DD0-DD7 and DA0-DA4. To display a selected ASCII character, the CPU U9 puts data describing the character on the DD0-DD7 (P3.0-P3.6 outputs of the CPU U9) bus. The CPU U9 transmits a low signal ENABLE (DWR) to segment decoder U10, which decodes bits DA2-DA4 and applies a low enable signal to the appropriate ones of display device U1-U8. The enabled display device then decodes the character select bit DA0 and DA1 to select the character position which displays the ASCII character defined by data bus DD0-DD6. As with the LEDs, the biopsy needle positioning motor controller defines the brightness of the position readout display. The biopsy needle positioning motor controller communicates the brightness level to the CPU U9, which then switches the BRIGHTNESS (BL) signal on and off, producing the designated duty cycle.

Figure 6:
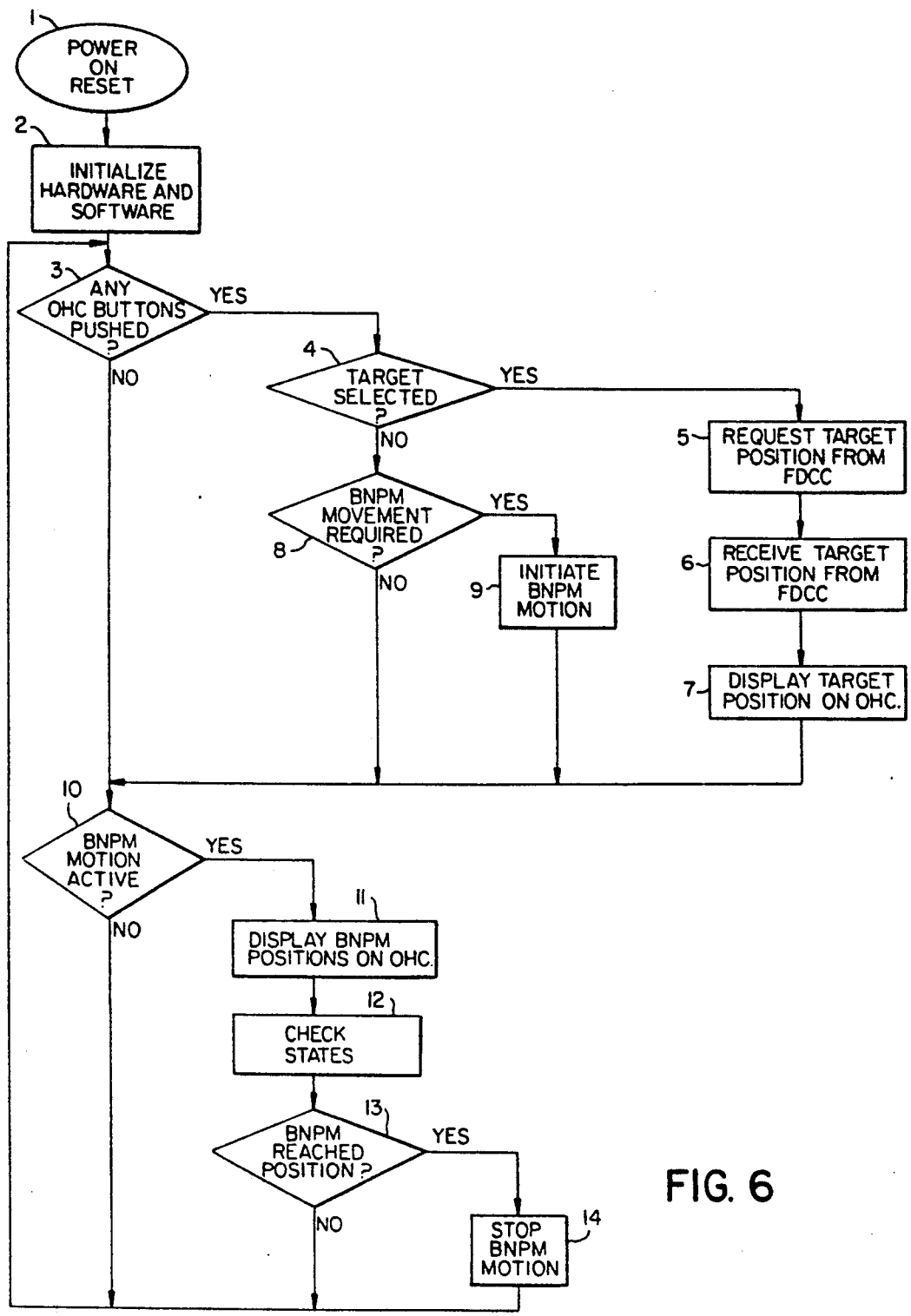
FIG. 6 is a flow chart of the software program executed by the biopsy needle positioning motor controller of FIGS. 1 and 3.

Referring now to FIG. 6, there is shown a flow chart of the principal software program performed by the biopsy needle positioning motor controller. All of the software represented by the flow chart of FIG. 6 is stored in EPROMs U1 and U6 of the biopsy needle positioning motor controller and is conventionally written in 8051 assembly language. In accordance with block 1 of the flow chart, the software performs several tasks on initialization of the motorized biopsy needle positioner. When power is first applied to the system, the reset circuit U23 within the biopsy needle positioning motor controller applies a CPU reset pulse to the 8032 CPU (U18). This reset pulse drives the 8032 CPU to its intialization routine.

In accordance with block 2 of the flow chart of FIG. 6, following the power on reset, the 8032 CPU initiates power on reset diagnostics (PRD) which are a series of low level tests of the system hardware to determine whether or not the hardware is working well enough to permit operation to continue. If the power on diagnostics are executed successfully, the 8032 CPU begins performing a number of hardware and software initialization tasks. These include 1) initializing the input/output (I/O) ports on the operator hand controller and biopsy needle positioning motor controller; 2) setting the output ports on the operator hand controller and biopsy needle positioning motor controller to default conditions; 3) clearing the input ports and memory locations of RAM 15 in the biopsy needle positioning motor controller; 4) resetting smart controllers U16 and U17 within the biopsy needle positioning motor controller and loading control parameters; 5) reading the operating program stored in EEPROMs U1 and U6 into the RAM portion of memory U15; 6) setting up the 8032 CPU internal timer 1 for 10-msec periodic interrupt; 7) setting up the 8032 CPU internal timer 0 for 9600 baud rate; 8) setting up the 8032 internal universal asynchronous receiver/transmitter (UART) for debug terminal/remote display; 9) initialization of dual UART (DUART U20) in the biopsy needle positioning motor controller for serial data transfers; and 10) performing miscellaneous variable initialization as required.

In accordance with block 3 of the flow chart of FIG. 6, following initialization, the 8032 CPU checks the condition of the key state byte sent by the operator hand controller via serial communication channel A and stored in RAM U15. If the operator hand controller has sent an INT0 byte indicating that a key has been depressed, the software branches to interrogation block 4. If no keys have been depressed, the software increments to interrogation block 10.

In accordance with block 4 of the flow chart of FIG. 6, the 8032 CPU checks the key state byte stored in RAM U15 to determine if the key depressed is the TARGET key. If so, the software branches to routine block 5. If the TARGET key has not been depressed, the software increments to interrogation block 8.

In accordance with block 5 of the flow chart of FIG. 6, the 8032 CPU sends a request for the spatial coordinates of the identified point of interest within the patient's breast to the film digitizer and coordinates calculator via serial comunications channel B and through DUART U20. The software then increments to routine block 6.

In accordance with block 6 of the flow chart of FIG. 6, the film digitizer and coordinates calculator responds to a request for spatial coordinates by sending a formatted data package containing those spatial coordinates. This data package is automaticaly stored in the XDATA buffer section of RAM U15. The software then increments to routine block 7.

In accordance with block 7 of the flow chart of FIG. 6, the 8032 CPU initiates position display on the operator hand controller by storing the data package containing the spatial coordinates of the identified point of interest in the XDATA buffer of RAM U15. The main program initiates transfer of the first character of the display, via serial data communications channel A, and then turns the data transfer task over to an interrupt handler subroutine which completes transfer of the remaining 31 characters of displayed information. When the transfer is complete, the software increments to interrogation block 10.

In accordance with block 8 of the flow chart of FIG. 6, the 8032 CPU checks the key state byte from the operator hand controller to determine if one of the direction arrow keys or the OFFSET key has been depressed, thereby requiring movement of the biopsy needle positioning mechanism. If so, the software branches to routine block 9. If not, the software increments to interrogation block 10.

In accordance with block 9 of the flow chart of FIG. 6, the 8032 CPU loads "go to" data in the motor control circuits for each of the rotation, angulation, and depth axes of the biopsy needle positioning mechanism that represents the current identified point of interest with the patient's breast. In addition to the position data, the 8032 CPU issues start and enable commands to the smart motor controllers U16 and U17. The program then increments to interrogation block 10.

In accordance with block 10 of the flow chart of FIG. 6, the software monitors the feedback position data from the smart motor controllers U16 and U17 to determine if the biopsy needle positioning mechanism is moving. If no movement is detected, the software branches back to the beginning of the main program loop at interrogation block 3, and the 8032 CPU issues a program loop pulse to the reset circuit. If movement of the biopsy needle positioning mechanism is detected, the program branches to routine block 11.

In accordance with block 11 of the flow chart of FIG. 6, the program monitors the motor position data from the smart motor controllers U16 and U17 on each axis. The new position data is loaded into the XDATA buffer in RAM U15 and the first character is transferred to the operator hand controller via serial communications channel A by the main program. The remaining characters are then transferred by the interrupt handler subroutine. The program then increments to routine block 12.

In accordance with block 12 of the flow chart of FIG. 6, the program checks all status and error information to determine 1) whether any axis has reached a soft limit; 2) whether any axis has reach a hard limit; or 3) whether any current limit been reached. In addition, the smart controller status is checked to determine 1) whether an excessive position error exists; 2) whether a wraparound error has occurred; or 3) whether an index (center 0) has been detected. The program then increments to interrogation block 13.

In accordance with block 13 of the flow chart of FIG. 6, the 8032 CPU compares current position data to the coordinates of the indentified point of interest to determine if the biopsy needle positioning mechanism is properly positioned for insertion of the biopsy needle to the identified point of interest. If it is not at the correct position, the program loops back to interrogation block 3 and the 8032 CPU issues a program loop pulse to the reset circuits. If the biopsy needle positioning mechanism has reached the target position, the program branches to routine block 14.

In accordance with block 14 of the flow chart of FIG. 6, the 8032 CPU issues a status byte to the smart motor controllers U16 and U17 for each axis, causing the motors to stop. The program then loops back to interrogation block 3, and the 8032 CPU issues a program loop pulse to the reset circuits.

As described in detail above, the software flowcharted in FIG. 6 controls the high level modes of operation of the motorized biopsy needle positioner of the present invention. These modes of operation include the JOG mode that enable manual control of the motion of the biopsy needle, the HOME mode that places the biopsy needle in the HOME position, the TARGET mode that drives the biopsy needle into position for insertion to the identified point of interest within the patient's breast, the OFFSET mode that drives the biopsy needle into position for insertion to a point within the patient's breast that is spatially offset from the identified point of interest, and the ERROR mode in which certain error messages are visually displayed to the user. In controlling the modes of operation described above, the software of FIG. 6 processes key commands received from the operator hand controller, generates messages to be display on the operator hand controller, issues requests to the film digitizer and coordinates calculator for data relating to the spatial coordinates of the identified point of interest, processes data received from the film digitizer and coordinates calculator, issues commands for controlling movement of the biopsy needle positioning mechanism, and performs state machine type processing.

In addition, the software flowcharted in FIG. 6 performs motion control by receiving commands from the mode control logic, by generating commands to the smart motor controllers U16 and U17 within the biopsy needle positioning motor controller, and by monitoring status during movement of the biopsy needle positioning mechanism. The current motor positions and status information is updated as required for the mode control logic to track the movement of the biopsy needle positioning mechanism. Finally, the software periodically sends messages for display on the remote view and display box. These messages are collected by the interrupt service routine and stored in RAM U15.

In operation, the clinician user initiates a breast biopsy procedure by employing the film digitizer and coordinates calculator to digitize an identified point of interest within the patient's breast and to then compute the spatial coordinates of that identified point of interest. The computed spatial coordinates appear in the displays of the film digitizer and coordinates calculator, the remote view and display box, and the operator hand controller. The user then employs the operator hand controller to automatically set the biopsy needle positioning mechanism such that the biopsy needle retained therein is precisely positioned for insertion to the identified point of interest by simultaneously depressing the ENABLE and TARGET keys on the operator hand controller. Once the identified point of interest has been sampled, the user may wish to take a biopsy of the surrounding tissue. This is accomplished by entering offsets in as many of the three coordinate axes (rotation, angulation, and depth) as desired. Offsets of 1 to 20 millimeters, in 1-millimeter increments, may be entered by the user. To enter an offset, the user employs the film digitizer and coordinates calculator to place the mouse on one of the stereotactic images of the patient's breast and moves the crosshairs of the mouse above, below, to the right, or to the left of the identified point of interest. The user then clicks the mouse button once for each millimeter of offset desired in that direction. The three displays track the offset entered by the user and display the number of millimeters of offset. The user must simultaneously depress the ENABLE and OFFSET keys on the operator hand controller to move the biopsy needle positioning mechanism to the offset location. After that biopsy is completed, the user may enter a new offset and repeat the above procedure to obtain a biopsy at another point that is also spatially offset from the original identified point of interest. Alternatively, the biopsy needle positioning mechanism may be returned to the position required for insertion of the biopsy needle to the original identified point of interest by simultaneously depressing the ENABLE and TARGET keys of the operator hand controller.

The user may disregard the identified point of interest and instead select a manual mode of operation to move the biopsy needle positioning mechanism as desired by first simultaneously depressing the ENABLE and MANUAL keys of the operator hand controller. This enables the four directional arrow keys of the operator hand controller, which may then be actuated to provide manual control of the rotation and angulation axes of the biopsy needle positioning mechanism. The user simultaneously depresses the ENABLE key and one of the directional arrow keys to drive the biopsy needle positioning mechanism in the desired direction. The three displays track this movement to provide a visual display of the movement of the biopsy needle positioning mechanism as it occurs. To return the biopsy needle positioning mechanism to the position required for insertion of the biopsy needle to the original identified point of interest within the patient's breast under examination, it is only necessary for the user to simultaneously depress the ENABLE and TARGET keys.

I claim:

1. An apparatus for use in inserting a biopsy needle to a point of interest within a patient's captive breast, comprising:
   (a) biopsy needle positioning means for controllably retaining a biopsy needle for movement within a spatial coordinate system that encompasses a patient's captive breast, the biopsy needle positioning means including motorized means for positioning said biopsy needle in accordance with at least one specified coordinate of the spatial coordinate system;
   (b) controller means, coupled to said biopsy needle positioning means, for receiving coordinate information that specifies at least one coordinate of a point of interest within said patient's captive breast;
   (c) first user control means, coupled to said biopsy needle positioning means, for enabling a user to initiate automatic movement of said biopsy needle in accordance with coordinate information received by said controller means and
   (d) offset control means for controlling said biopsy needle positioning means to move said biopsy needle in accordance with offset coordinate information regarding an offset point that is spatially offset from said point of interest so as to permit insertion of said biopsy needle to the offset point within the patient's captive breast.

2. The apparatus of claim 1, wherein said first user control means includes display means for visually displaying coordinate information that specifies coordinates of said point of interest in the patient's captive breast.

3. The apparatus of claim 1, wherein said first user control means includes display means for visually displaying offset coordinate information that specifies coordinates of said offset point within the patient's captive breast.

4. The apparatus of claim 1, further comprising:
   safety interlock means, actuable by the user, for preventing inadvertent movement of said biopsy needle.

5. The apparatus of claim 1, wherein said controller means is operative for receiving coordinate information in the form of horizontal angle, vertical angle, and insertion depth distance to specify coordinates of said point of interest within the patient's captive breast.

6. The apparatus of claim 1, wherein the controller means is operative for receiving coordinate information in the form of x, y, and z rectangular axes distances to specify coordinates of said point of interest within the patient's captive breast.

7. The apparatus of claim 1, further comprising:
   second user control means, coupled to said biopsy needle positioning means, for enabling a user to initiate manual movement of said biopsy needle responsive to input from the user.

8. The apparatus of claim 1, further comprising:
   directional control means for designating movement of said biopsy needle in one or more selected directions.

9. The apparatus of claim 8, wherein the directional control means comprises up, down, left, and right arrow keys.

10. The apparatus of claim 8, further comprising:
    display means for visually displaying coordinate information corresponding to the position of said biopsy needle as it moves in the one or more selected directions in response to actuation of directional control means.

11. The apparatus of claim 1, further comprising:
    driven retaining means for retaining and driving said biopsy needle within the patient's breast to obtain a tissue sample from said point of interest.

12. The apparatus of claim 1, further comprising:
    immobilizing means for immobilizing the patient's breast relative to said spatial coordinate system.

* * * * *